(12) United States Patent
Rake et al.

(10) Patent No.: US 9,820,685 B2
(45) Date of Patent: Nov. 21, 2017

(54) MEASUREMENT DEVICE TO CAPTURE VITAL PARAMETERS

(71) Applicant: ZF Friedrichshafen AG, Friedrichshafen (DE)

(72) Inventors: Ludger Rake, Steinfeld (DE); Andreas Giefer, Lemfoerde (DE); Joerg Meyer, Wagenfeld (DE)

(73) Assignee: ZF Friedrichshafen AG, Friedrichshafen (DE)

( * ) Notice: Subject to any disclaimer, the term of this patent is extended or adjusted under 35 U.S.C. 154(b) by 0 days.

(21) Appl. No.: 14/357,469

(22) PCT Filed: Nov. 16, 2012

(86) PCT No.: PCT/EP2012/072867
§ 371 (c)(1),
(2) Date: May 9, 2014

(87) PCT Pub. No.: WO2013/076018
PCT Pub. Date: May 30, 2013

(65) Prior Publication Data
US 2014/0316227 A1 Oct. 23, 2014

(30) Foreign Application Priority Data
Nov. 21, 2011 (DE) .................. 10 2011 086 740

(51) Int. Cl.
*A61B 5/00* (2006.01)
*A61B 5/1455* (2006.01)
(Continued)

(52) U.S. Cl.
CPC .............. *A61B 5/18* (2013.01); *A61B 5/0059* (2013.01); *A61B 5/0295* (2013.01);
(Continued)

(58) Field of Classification Search
CPC ....... A61B 5/02; A61B 5/024; A61B 5/02416; A61B 5/02427; A61B 5/0245;
(Continued)

(56) References Cited

U.S. PATENT DOCUMENTS 4,706,072 A * 11/1987 Ikeyama .................. A61B 5/18
600/476
6,104,296 A * 8/2000 Yasushi .............. A61B 5/04085
600/301

(Continued)

FOREIGN PATENT DOCUMENTS

DE   10 2005 007963 A1   8/2006

OTHER PUBLICATIONS

German Office Action for DE 10 2011 086 740.6, dated Jul. 26, 2012 (German Language), 5 pages.
(Continued)

*Primary Examiner* — Eric Winakur
(74) *Attorney, Agent, or Firm* — Brinks Gilson & Lione

(57) ABSTRACT

The invention concerns a measurement device to capture at least one vital parameter of a person in a motor vehicle with a steering wheel. The measurement device includes a finger sensor device with an optical sensor device, where the finger sensor device is attached to the steering wheel in the transition zone between a steering wheel spoke and the hub of the steering wheel.

19 Claims, 3 Drawing Sheets

Figure 1:
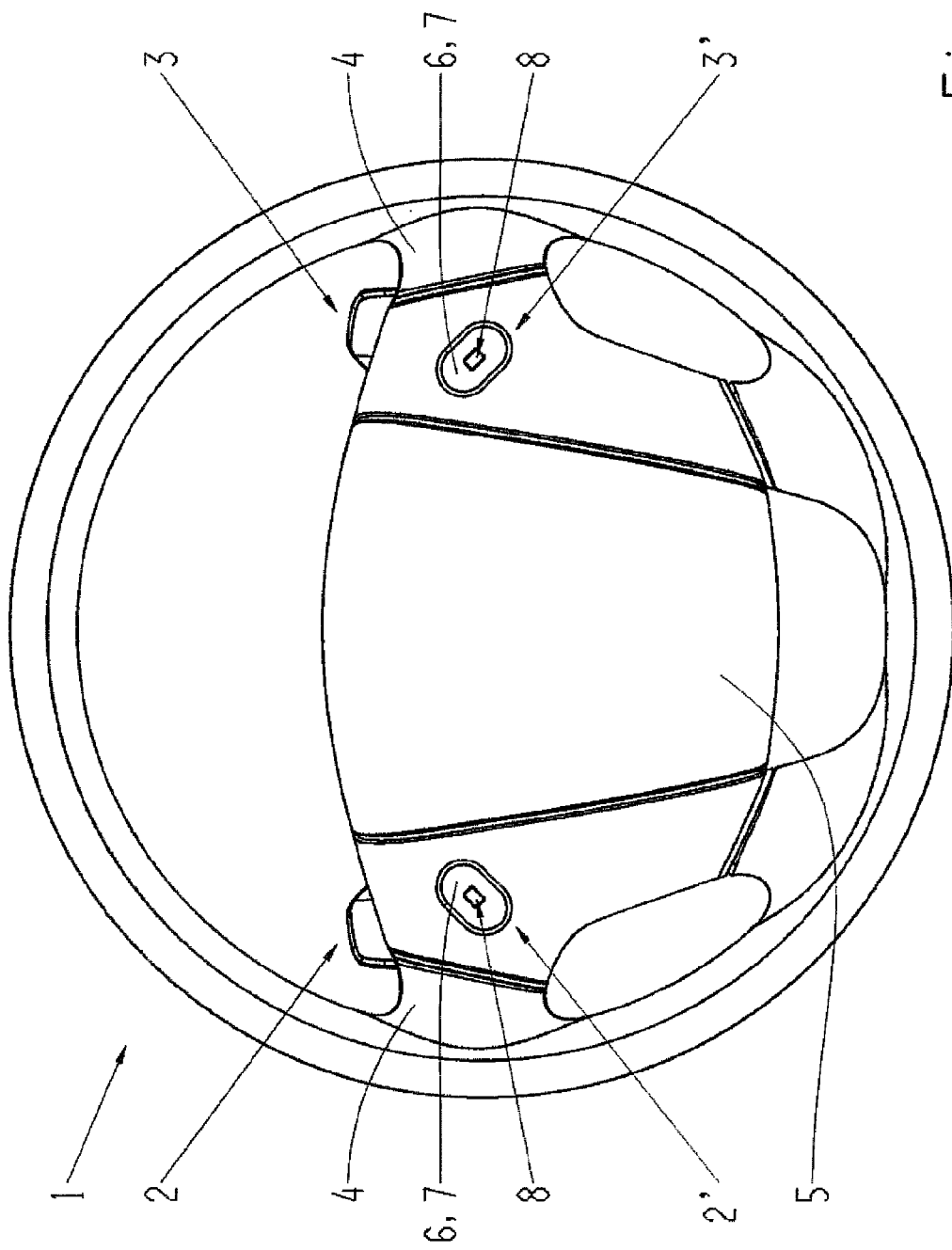

(51) Int. Cl.
  *B60W 40/08* (2012.01)
  *A61B 5/18* (2006.01)
  *B62D 1/04* (2006.01)
  *A61B 5/0295* (2006.01)
  *A61B 5/0402* (2006.01)
  *A61B 5/024* (2006.01)
  *A61B 5/0404* (2006.01)

(52) U.S. Cl.
  CPC ........ *A61B 5/0402* (2013.01); *A61B 5/14551* (2013.01); *A61B 5/6826* (2013.01); *A61B 5/6893* (2013.01); *B62D 1/046* (2013.01); *A61B 5/02433* (2013.01); *A61B 5/02444* (2013.01); *A61B 5/0404* (2013.01); *B60W 2040/0872* (2013.01)

(58) Field of Classification Search
  CPC . A61B 5/0402; A61B 5/1455; A61B 5/14551; A61B 5/14552; A61B 5/6893; B60W 40/08; B60W 2040/0818; B60W 2040/0836; B60W 2040/0872; B60K 28/06
  See application file for complete search history.

(56) References Cited

U.S. PATENT DOCUMENTS

| | | | | |
|---|---|---|---|---|
| 6,239,707 | B1* | 5/2001 | Park | A61B 5/18 600/301 |
| 6,575,902 | B1* | 6/2003 | Burton | A61B 5/18 600/300 |
| 6,731,925 | B2* | 5/2004 | Naboulsi | B60R 11/02 340/575 |
| 2006/0025698 | A1 | 2/2006 | Nakagawa et al. | |
| 2008/0238695 | A1 | 10/2008 | Yanai et al. | |
| 2009/0163787 | A1* | 6/2009 | Mannheimer | A61B 5/14552 600/324 |
| 2011/0061488 | A1* | 3/2011 | Walters | F16H 59/02 74/552 |
| 2011/0237912 | A1* | 9/2011 | Couronne | A61B 5/14551 600/323 |
| 2011/0245643 | A1 | 10/2011 | Lisseman et al. | |
| 2012/0004818 | A1* | 1/2012 | Wakita | F16H 59/0204 701/66 |
| 2013/0110311 | A1* | 5/2013 | Ver Steeg | A61B 5/14546 701/1 |

OTHER PUBLICATIONS

International Search Report and Written Opinion from corresponding International Patent Application PCT/EP2012/072867, dated Mar. 25, 2013 (German Language), 13 pages.

International Search Report dated Mar. 25, 2013 in International Application No. PCT/EP2012/072867 (English Language), 3 pages.

Futatsuyama et al., "Noise Robust Optical Sensor for Driver's Vital Signs", SP-2299, SAE 2011 World Congress & Exhibition, Apr. 12, 2011 (Apr. 12, 2011), pp. 119-125, XP009167777, Abschnitte "Overview of our steering wheel sensor" and "Techniques to improve SNR under noisy conditions".

Hanbit Park et al., "Drowsy driving detection based on human pulse wave by Photoplethysmography Signal Processing", Proceedings of the $3^{rd}$ International Universal Communication Symposium (IUCS '09), Jan. 1, 2009 (Jan. 1, 2009), pp. 89-92, XP055055678, New York, New York, USA, DOI:10.1145/1667780.1667798, ISBN: 978-1-60-558641-1.

Stephan Heuer et al., "Unobtrusive in-vehicle biosignal instrumentation for advanced driver assistance and active safety" 2010 IEEE EMBS Conference on Biomedical Engineering and Science (IECBES 2010), Nov. 30, 2010 (Nov. 30, 2010), pp. 252-256, XP031936758, DOI: 10.1109/IECBES.2010.5742238 ISBN: 978-1-4244-7599-5.

* cited by examiner

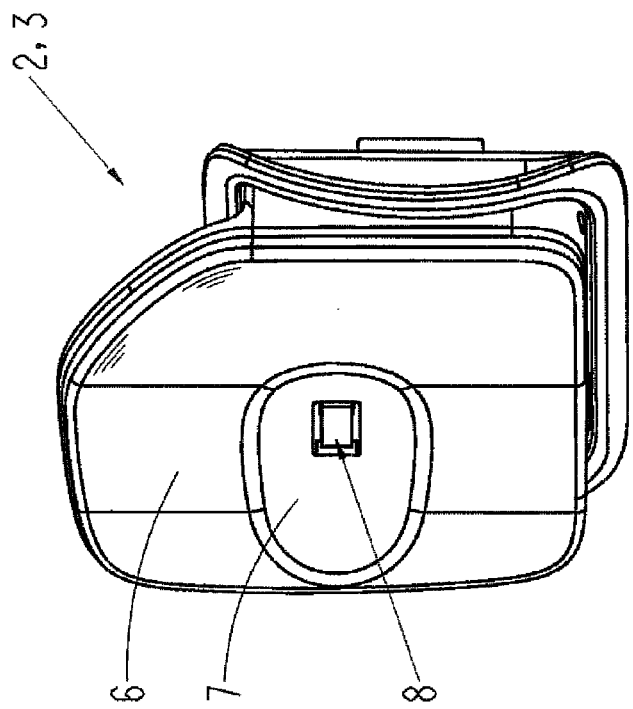
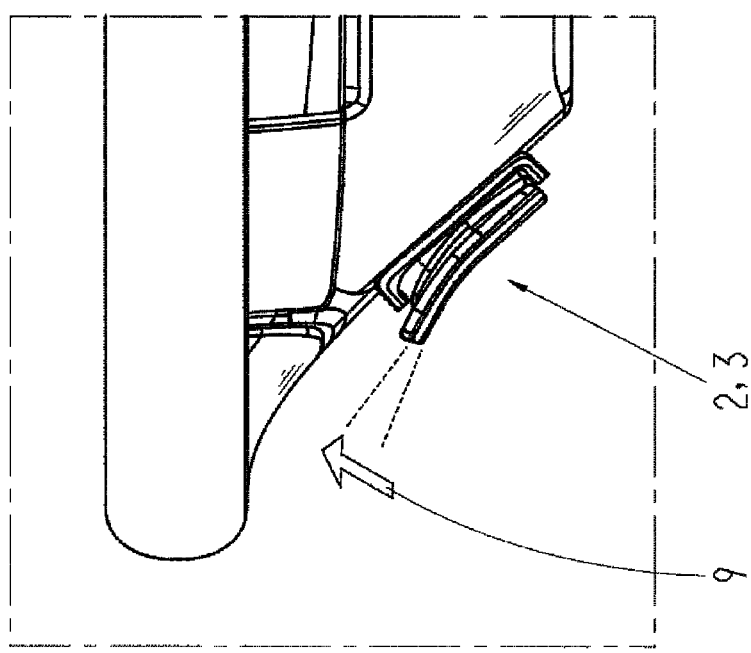

MEASUREMENT DEVICE TO CAPTURE VITAL PARAMETERS

This application is a filing under 35 U.S.C. §371 of International Patent Application PCT/EP2012/072867, filed Nov. 16, 2012, and claims the priority of DE 10 2011 086 740.6, filed Nov. 21, 2011. These applications are incorporated by reference herein in their entirety.

The invention relates to a device to capture at least one vital parameter of a person in a motor vehicle, in accordance with the preamble of Patent claim 1.

The capture of vital parameters of persons by means of optical plethysmography (measurement of changes in volume) and pulse oxymetry (measurement of oxygen saturation) by themselves is known and is normally handled by means of non-invasive measurements in particular of the pulse rate, the variability of the pulse rate and the arterial oxygen saturation by measurement of light absorption or light reflection when light passes through tissue.

Plethysmography and pulse oxymetry are based on fundamentally similar optical measurement processes. Plethysmography uses the optical measurement of changes in light absorption resulting from changes in volumes, specifically of blood vessels, whereas pulse oxymetry is based on the differential absorption or reflection of light—which depends on the blood oxygen saturation level—of red and infrared measurement light beams passing through skin and tissue.

Pulse oxymetry normally measures the oxygen saturation values (SPO2 values) by an optical sensor on a finger, toe or ear lobe, where the measurement is taken by a clip-on sensor or glue-on sensor. The sensors normally consist of one or two light sources, such as embodied as a red light-emitting diode and/or an infrared diode, connected to a photo sensor or a photo diode. The infrared diode emits rays in the invisible range of the electromagnetic spectrum, whereas the red diode emits light in the visible range.

The different color of blood hemoglobin more or less saturated with oxygen generates different degrees of absorption of the transmitted red light or infrared light that are captured by the photo sensor. The measurement unit can then capture or determine the oxygen saturation of the blood in the capillaries—for example, by comparing the measurement values to a reference table. In addition to the oxygen saturation, the optoelectronic sensor unit can generally also measure the pulse or the pulse wave, the pulse rate and the variability of the pulse rate.

In this regard, optical plethysmography and pulse oxymetry are a normal component of medical life, and they are used for the normal monitoring of patients as well as for diagnostic purposes. Among other uses, pulse oxymetry is also increasingly used for "home care," namely for health monitoring of patients in a home setting, for example. This includes in particular the care of patients with cardiac risk factors and the diagnosis of sleep disturbances as well as the determination of instances of fatigue or stress.

However, the use of optical plethysmography (measurement of changes in volume) and pulse oxymetry (measurement of oxygen saturation) to capture the specified vital parameters of patients or persons may be applied not only in stationary conditions or in a hospital, but also, for example, while driving a car or motor vehicle.

Mobile devices are known for such non-stationary measurements primarily where sensors will be attached directly to the body. However, this limits the freedom of movement of the patients, such that these types of applications or devices are often not acceptable solutions, specifically not in an automobile. In order to address the problem of limited freedom of movement in an automobile setting, attempts have been made to integrate the specified optical sensors in the control devices of the motor vehicle. In each case, the goal is the capture of vital parameters with minimal impact on the driver.

DE 10 2008 056 250 A1 teaches the incorporation of optical sensors for plethysmography or pulse oxymetry in a shift knob of a motor vehicle. This solution known in the state of the art requires the driver to undertake the measurement by initially removing a hand from the steering wheel, which may result in measurements that are not taken as frequently or as regularly as may be desirable to monitor the driver's health status. Thus, the proposal had been made to incorporate optical sensors for the specified measurement processes in the rim of the steering wheel of a motor vehicle. However, placement in the rim of a steering wheel often provides for a poor quality signal of the optical measurement, specifically due to the cramped space, the potentially high variability of brightness due to the proximity to the windshield and due to the difficulty of replicating the proper position of the fingers of the driver for the measurement.

The state of the art also includes measurement processes to take electrocardiogram (EKG) measurements in a moving automobile—in place of or in addition to plethysmographic or pulse oxymetric measurements. Attempts have been made here to place the required EKG electrodes on the steering wheel, specifically in the upper segment of the rim of the steering wheel. However, this arrangement also presents disadvantages regarding the design of the steering wheel and in fluctuations of the measurements when sun radiation heats the steering wheel or the EKG sensors to high temperatures.

The present invention is intended to provide a device to capture vital parameters that overcomes the listed disadvantages or limitations. The invention is intended to provide specifically for a reliable and operationally robust integration of the measurement sensors to determine the blood oxygen saturation, the pulse parameters and/or the EKG of a driver of a motor vehicle. In particular, the invention is intended to overcome the listed disadvantages of the attachment of the measurement sensors to the shift knob of the motor vehicle and/or to the rim of a steering wheel.

Towards this goal, the present invention proposes a measurement device with the characteristics listed in Patent claim 1.

Preferred embodiments are presented in the dependent claims.

The measurement device of the present invention serves to capture at least one vital parameter of a person in a motor vehicle. To this end, the measurement device includes at least one finger sensor device with at least one optical sensor device, where the sensor device includes at least a first light source and at least one light-sensitive element.

The measurement device is characterized by having the finger sensor device attached to the steering wheel in the transition zone between a steering wheel spoke and the main body or hub of the steering wheel.

A steering wheel is usually constructed in such a way that the steering wheel body or steering wheel impact absorber or steering wheel hub arranged in the center of the steering wheel is provided for connection to a steering column for transmitting the steering movement carried out with the steering wheel to the steering column, wherein the steering wheel body is connected via steering wheel spokes to a usually circular steering wheel rim which runs around the steering wheel body at a distance. The steering wheel body is usually provided to accommodate an activation device which is embodied as a horn and, depending on the design of the motor vehicle, a driver airbag. The steering wheel rim forms an activation element for the vehicle driver or drive for receiving and transmitting the desired steering movement. The steering movement which is applied to the steering wheel rim is transmitted to the steering wheel body and via the latter to the steering column via one or more steering wheel spokes which are configured as a rigid connection between the steering wheel rim and the steering wheel body.

Furthermore, customary steering wheels are known to have operative control elements in the form of pushbutton keys or switches for performing the remote control of a radio device, of a navigation device, of an air-conditioning system, of an on-board computer, of a cruise controller device, of a hands-free speaking system or of some other operator control device. In other words, by means of the operator control elements arranged on the steering wheel it is made possible for the driver to perform the operator control of the respective operator control device without having to take his hand away from the steering wheel or having to change a standard position of the hands on the steering wheel. As a result, customary distraction of the driver which is otherwise entailed by operator control of the respective operator control devices being performed directly on the device can be minimized.

The pushbutton key and/or switch are usually arranged on the side of the steering wheel body, in other words on the steering wheel body in the intermediate space between the steering wheel body and the steering wheel rim. Alternatively or additionally, such pushbutton keys and switches can be arranged in a junction region extending between the steering wheel body and the steering wheel spoke. The steering wheel spoke extends here from the steering wheel rim in the direction of the steering wheel body and is rigidly connected to the steering wheel body by means of the junction region. The junction region can form part of the steering wheel spoke and/or part of the steering wheel body on the component side. In other words, the junction region can form an end region of the steering wheel spoke, which end region is adjoined by the steering wheel body, or an end region of the steering wheel body, which end region is adjoined by the steering wheel spoke, wherein the steering wheel spoke and the steering wheel body are connected to one another. It is also conceivable that one part of the junction region is formed by the steering wheel spoke and the other part of the junction region is formed by the steering wheel body, wherein the steering wheel spoke and the steering wheel body adjoin one another in the junction region and are connected to one another. The junction region is characterized here by the property that one or more operator control elements for performing the remote control of operator control devices such as, for example, the above-mentioned ones, are arranged or can be arranged in the junction region, wherein the operator control of the operator control element or elements can be performed by the driver without letting go of the steering wheel, and more preferably without changing the standard position of his hands on the steering wheel.

Placement of the finger sensor device on the steering wheel in the transition zone between a steering wheel spoke and the main body of the steering wheel has the advantage that the driver no longer needs to remove the hand from the steering wheel in order to determine the vital parameter in question, thus, for example, determining the blood oxygen saturation or the pulse, and to move the hand to a sensor on the shift knob, for example. Rather, thanks to the invention, the measurement of the vital parameter(s) can be handled with a minimum of effort merely by contact of a finger, for example, with the finger sensor device on the steering wheel. Placement of the finger sensor device in the transition zone between a steering wheel spoke and the main body also has the advantage that the measurement can be taken without removing the hand from the rim of the steering wheel.

The thus simplified measurement method facilitates more convenient and thus more frequent and regular measurements, which may be of significance for patients with corresponding risk factors.

Placement of the finger sensor device on the steering wheel in the transition zone between a steering wheel spoke and the main body or hub of the steering wheel has the added advantage that this segment of the steering wheel is not normally a segment heated by direct radiation from the sun, which will reduce the impact of irrelevant radiation on the sensor, which is a factor in the state of the art, or the significant heating of the contact surfaces on the steering wheel, which is likewise a factor in the state of the art.

The finger sensor device may be positioned here in particular such that the sensor surfaces in question may be accessible even in the normal contact position of the hands of the driver without additional hand movements. This will facilitate the measurement with minimal added effort, thus increasing the efficiency of the measurement of the vital parameter.

Preferred embodiments may have the finger sensor device on the rear of the steering wheel away from the driver set up for contact with at least one finger (but not the thumb) or the finger sensor device may be placed on the front of the steering wheel facing the driver set up for contact with a thumb. In either case, contact of the finger or the thumb with the finger sensor device can be made without removing the hand from the steering wheel and without releasing the rim of the steering wheel.

The invention can be realized regardless of the details of the construction of the finger sensor device and regardless of its contact with the steering wheel, as long as the finger sensor device is placed in the transition zone between the steering wheel spoke and the hub of the steering wheel on the rear of the steering wheel. A particularly preferred embodiment of the invention places the finger sensor device in a sensor surface area attached such that the surface can be depressed with pressure against the steering wheel body.

Placement of the finger sensor device such that the sensor surface can be depressed is particularly advantageous in that this method assures reliable and reproducible contact of one or more fingers of the driver on the sensor surface, because the spring action of the sensor surface gives the driver direct feedback on whether the contact pressure of one or more fingers on the sensor surface is sufficient.

The invention can also be embodied regardless of the design details of the spring action of the sensor surface on the steering wheel.

Thus, for example, a single-piece design of the sensor surface elastically attached to the steering wheel cover is conceivable. A particularly advantageous embodiment of the invention provides for unambiguous and reproducible feedback regarding the proper contact pressure on the sensor surface by means of a toggle switch in the sensor surface. This design provides an exact determination of the contact pressure and the contact path of the spring action on the sensor surface on the steering wheel, such that both pressure and path are permanently reproducible. The toggle switch will preferably also be designed such that an activation, i.e. activating pressure on the switch, will also automatically initiate the measurement process. This will also assure that the measurement will be undertaken only if there is sufficient pressure of the finger(s) on the measurement sensors.

Another preferred embodiment of the invention uses a design where the sensor surface includes at least one recessed finger depression into which at least one fingertip or thumb tip will be inserted. The optical sensor device is attached to the recessed finger depression. The recessed finger depression on the sensor surface and the associated sensor device will improve also the sensation that the finger makes proper contact with the sensor, thus further improving the reliability of the measurement of the vital parameters.

Another particularly preferred embodiment of the invention provides for an essentially paddle-shaped sensor surface. This will facilitate the simultaneous contact of several fingers of a hand, thus improving the comfort of contact with the steering wheel, particularly so when the fingers of the hand make contact with the sensor surface over long periods of time. The sensor surface will preferably contain an electrically conducting surface with an evaluation device to generate an EKG.

Apart from the measurement or monitoring of pulse values or blood oxygen values, this embodiment will also generate an EKG of the driver, which will provide an even more reliable capture or the related monitoring of the vital parameters and thus of the health status of the driver.

Another particularly preferred embodiment of the invention provides for a measurement device with two finger sensor devices on the steering wheel, each of which is designed for a hand of the driver and which are placed symmetrically on the steering wheel. This permits a further improvement of the reliability and precision of the measurement of the vital parameters—such as by deriving average values. The presence of two sensor devices also improves the EKG measurements.

Another preferred embodiment of the invention includes a first light source to generate light in the visible wave length range within the optical sensor device in addition to the light-sensitive element and a second light source to generate light in the invisible wave length range, specifically in the infrared wave length range. This alternative will extend the measurement of vital parameters by the measurement device of the invention to measurements of the volume of vessels, specifically optical plethysmography, as well as measurements regarding the blood constituents, specifically oxygen monitoring by means of optical pulse oxymetry.

Another embodiment of the invention designs the toggle switch to be an activation device for another function of the motor vehicle. Preferably the toggle switch is here a shifter for a gear shift system.

The specification whether an action or pressure on the toggle switch is a trigger for the measurement of the vital parameters or a trigger for another function, such as initiation of a shift in gears, can be handled in alternative ways. Thus, for example, pressure on one of two toggle switches could be interpreted in each case as an order to shift gears, whereas pressure on both toggle switches in the system could be interpreted in each case as an order to initiate measurement of the vital parameters. Alternatively, the steering wheel could also include another switch, where pressure on this switch by itself or in conjunction with subsequent or simultaneous pressure on the shift paddle(s) could be interpreted not as an order to shift, but as an order to commence measurement of the vital parameters.

The present invention can provide a measurement device that permits a reliable and comprehensive measurement and monitoring of vital parameters even while the vehicle is in motion without negative impacts on driving comfort or safety, specifically without forcing one hand to be removed from the steering wheel. The preferred design and placement of the finger sensor device will further facilitate a high precision of the measurement and minimal impacts from varying environmental conditions, such as light and temperature.

Further characteristics and advantages of the present invention derive from the following description of preferred embodiments of the invention, shown in drawings of the invention depicting preferred invention-relevant details, and from the patent claims. The individual characteristics may be embodied each by itself or in any combination with other characteristics in a variant of the invention.

Figure 2:
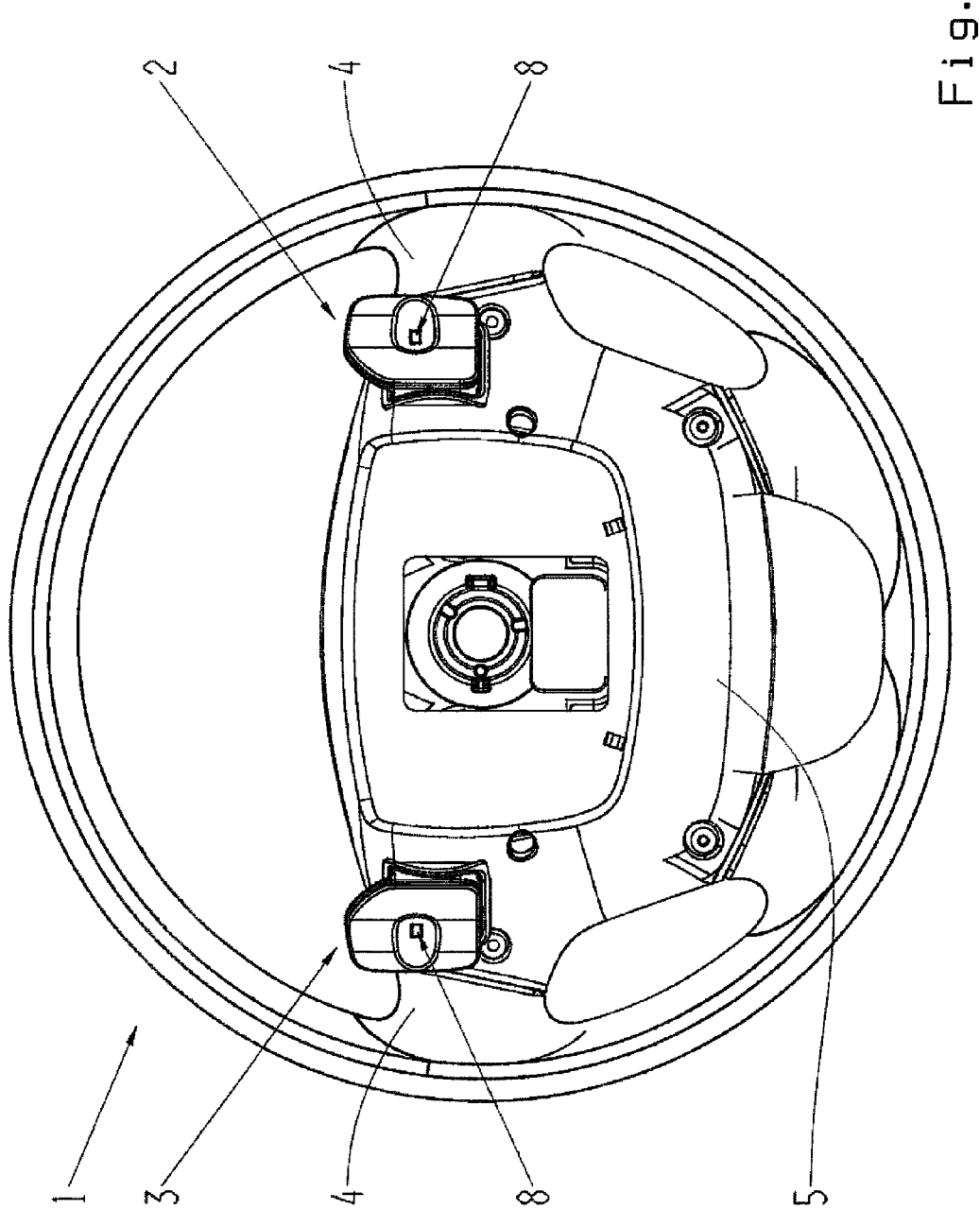

Preferred embodiments of the present invention are explained in more detail by means of the drawings shown below. They show:

FIG. 1 a frontal view of a steering wheel of a motor vehicle with a measurement device to capture vital parameters for a preferred embodiment of the present invention;

FIG. 2 a rear view of the measurement device for the steering wheel shown in FIG. 1;

FIG. 3 a close-up top view of the steering wheel with the measurement device of FIGS. 1 and 2; and FIG. 4 an enlarged isometric view of the sensor paddle of the measurement device of FIGS. 1 and 2.

FIGS. 1 and 2 depict a steering wheel 1 of a motor vehicle with a measurement device in a preferred embodiment of the present invention. A combination of FIGS. 1 and 2 show first that steering wheel 1 of the depicted embodiment has two finger sensor devices 2 and 3. Finger sensor devices 2 and 3 are here attached to the rear of the steering wheel away from the driver, in each case in the transition zone between steering wheel spoke 4 and the rear of the steering wheel body or steering wheel hub 5.

It can be seen that the position of sensor devices 2, 3 enable the required measurements of the vital parameters of the driver with a minimum of problems while the vehicle is moving, where it is not necessary to remove a hand from the steering wheel. The measurements may then normally be taken without changing the position of the hands on the steering wheel, because the steering wheel is normally held in the vicinity of the two horizontal spokes 4. Thus only the fingers need to make contact with the sensor devices, which are embodied here as sensor paddle 2, 3, in order to measure the vital parameters (if the fingers are not already there), and the measurement can then be initiated.

FIG. 3 shows an enlarged top view of one of the two sensor devices 2, 3 of steering wheel 1 of FIGS. 1 and 2 again in position, whereas FIG. 4 shows sensor device 2, 3 again separately in an isometric view. It can be seen here that sensor device 2, 3 in this embodiment of the invention consist of a toggle switch or switch paddle 2, 3, where the control surface 6 of toggle switch 2, 3 is simultaneously the contact surface for the fingers and contains in particular the recessed finger depression 7 to house the finger tip for the purposes of optical measurement of the vital parameters. Finger depression 7 contains thus an optical sensor device 8, which includes the LED or photo sensors needed for the measurement.

The capture or measurement of vital parameters is handled in the depicted embodiment of the invention by contact of preferably three fingers of a hand on control surface 6 of toggle switch(es) 2, 3, where the middle finger of the three rests in recessed finger depression 7, thus making direct contact with optical sensor device 8. The measurement itself is then effected by slight pressure on control surface 6 of toggle switch 2, 3, where toggle switch 2, 3 is depressed as indicated by arrow 9, which in turn initiates the measurement by tripping an electrical contact within toggle switch 2, 3.

Thus, there are two reasons why it is advantageous to integrate sensor device 8 in toggle switch 2, 3. First, the measurement is effected purposefully and at a specified time only if toggle switch 2, 3 is depressed. Second, the requirement that toggle switch 2, 3 is depressed—in order to initiate the measurement—itself assures a specific and close contact between the skin surface and measurement sensor 8 whenever there is intent to undertake a measurement.

Furthermore, in addition to the optical measurement of parameters related to the blood circulation status by means of optical sensor device 8, a simultaneous EKG measurement can be taken. Thus, surfaces 6 of toggle switches 2, 3 are embodied in metal or with a conductive surface. Consequently, the electronic evaluation of the contact current flowing between the finger surfaces and surfaces 6 of toggle switches 2, 3 can derive an electrocardiogram as an addition to the monitoring processes of the health status of the driver.

FIG. 1 also shows (in dashed lines) an alternative arrangement of sensor devices 2', 3' on the front of the steering wheel facing the driver. Sensor devices 2', 3' include here as well a conductive control surface 6 with an embedded finger depression 7, where the critical optical sensor device 8 is again contained within finger depression 7. In instances where sensor devices 2', 3' are placed on the front of the steering wheel facing the driver, sensor devices 2', 3' or the associated finger depressions 7 are formed or oriented such that the thumbs can easily be inserted into finger depressions 7 without requiring a change in the standard position of the hands on the steering wheel.

A further option (not depicted here) for the placement of sensor devices 2, 3 or 2', 3' places the sensor devices with their conductive control surfaces 6, finger depressions 7 and optical sensor devices 8 on the rim of the steering wheel such that the sensor devices can in each case make contact with one or more fingers without requiring the hands to be removed from the steering wheel or without changing the standard position of the hands on the steering wheel.

As a result, it is obvious that the invention presents a measurement device to capture vital parameters that facilitates a reliable measurement and monitoring of the vital parameters even while the automobile is in motion, while simultaneously—even during the measurement process—reducing or eliminating any negative impact on the driving comfort or safety.

REFERENCE NUMBERS

1 Steering wheel
2, 3 Finger sensor device, toggle switch, switch paddle
2', 3' Finger sensor device, toggle switch
4 Steering wheel spoke
5 Hub, steering wheel body
6 Sensor surface, control surface, EKG contact
7 Finger depression
8 Optical sensor device
9 Direction of pressure on toggle switch

The invention claimed is:

1. A device for measuring a health condition parameter of a user, the device comprising:
   a toggle switch with at least a depressed position; and
   a finger sensor comprising a finger sensor surface,
   wherein the finger sensor is configured to measure the health condition parameter when a finger of the user is placed on the finger sensor surface,
   wherein the toggle switch is configured to be installed on a steering wheel of a motor vehicle,
   wherein the finger sensor surface comprises at least a portion of an actuating surface of the toggle switch configured to ensure a reproducible contact pressure between the finger of the user and the finger sensor surface, and
   wherein the toggle switch is electrically connected with and sends an activation signal to a system in the motor vehicle, where the system performs a function other than initiating measurement of the health condition parameter when the toggle switch is depressed.

2. The device of claim 1, wherein the health condition parameter is a plethysmography parameter, a pulse oximetry parameter, or an electrocardiogram parameter.

3. The device of claim 1, wherein the finger sensor is installed in a transitional zone between a spoke and a hub of the steering wheel.

4. The device of claim 3, wherein the finger sensor is installed on a rear side of the steering wheel and faces away from the user, and wherein the finger sensor surface is positioned to make contact with a finger of the user when the user grasps the steering wheel at the transitional zone.

5. The device of claim 3, wherein the finger sensor surface is installed on a front side of the steering wheel and faces towards the user, and wherein the finger sensor surface is configured to be positioned to make contact with a thumb of the user when the user grasps the steering wheel.

6. The device of claim 1, wherein the finger sensor comprises an optical sensor located on the finger sensor surface, the optical sensor comprising:
   a light source configured to detect the health condition parameter when the user places a finger on the optical sensor; and
   a light-sensitive element configured to measure the health condition parameter.

7. The device of claim 6, wherein the light source is configured to generate visible light and invisible light, and the health condition parameter comprises blood vessel volume or blood constituents.

8. The device of claim 1, wherein the finger sensor comprises a finger depression recessed on the finger sensor surface and is fingertip-shaped so as to house a fingertip of the user, and wherein an optical sensor is located in the finger depression.

9. The device of claim 1, wherein the toggle switch is configured to initiate measurement of the health condition parameter when the toggle switch is depressed.

10. The device of claim 9, wherein the finger sensor surface is additionally configured to initiate measurement of the health condition parameter when the toggle switch is in a position other than the depressed position.

11. The device of claim 10, wherein the system in the motor vehicle is a gear shift system.

12. The device of claim 1, wherein the finger sensor surface comprises an electrically conductive surface connected to an electrocardiogram measurement device.

13. The device of claim 1,
   wherein the finger sensor surface comprises a left finger sensor surface and a right finger sensor surface, and
   wherein the left finger sensor surface and the right finger sensor surface are configured to be symmetrically located in opposite sectors of the steering wheel so that the left finger sensor surface is configured to contact a left-hand finger of the user and the right finger sensor surface is configured to contact a right-hand finger of the user.

14. The device of claim 1, the device including a first state and a second state,
   wherein in the first state, the finger sensor measures the health condition parameter when the finger of the user is placed on the finger sensor surface and the toggle switch is depressed,
   wherein in the second state, the system in the motor vehicle other than to initiate measurement of the health condition parameter is activated when the toggle switch is depressed, and
   wherein the device further comprises a second switch controlling whether the device is in the first state or the second state.

15. A method for measuring a health condition parameter of a user and activating a system of a motor vehicle with a toggle switch other than initiating measurement of the health condition parameter, the toggle switch including a finger sensor surface located on a driving wheel of a motor vehicle, wherein the finger sensor surface comprises an actuating surface of the toggle switch configured to ensure a reproducible contact pressure between the finger of the user and the finger sensor surface, the method comprising:
   measuring a health condition of a user when the finger sensor surface contacts a finger of the user while the user's finger is located on the driving wheel of the motor vehicle; and
   activating the system of the motor vehicle with the toggle switch when the toggle switch is depressed by the user during operation of the vehicle.

16. The method of claim 15, wherein measuring the health condition parameter comprises measuring a plethysmography parameter, a pulse oximetry parameter, or an electrocardiogram parameter.

17. The method of claim 15, further comprising:
   depressing the toggle switch connected to the finger sensor surface; and
   measuring the health condition parameter while the toggle switch is depressed.

18. The method of claim 15, wherein the system of the motor vehicle is a gear shift system.

19. A steering wheel of a motor vehicle, the steering wheel comprising:
   a steering wheel body;
   a device for measuring a health condition parameter of a user, the device comprising:
   a finger sensor comprising a finger sensor surface,
   wherein the finger sensor measures the health condition parameter when a finger of the user is placed on the finger sensor surface at least when the steering wheel is in a first state,
   wherein the finger sensor surface is installed on the steering wheel body,
   wherein the finger sensor surface comprises an actuating surface of a toggle switch configured to ensure a reproducible contact pressure between the finger of the user and the finger sensor surface,
   wherein the toggle switch is electrically connected with and sends an activation signal to a system in the motor vehicle, where the system performs a function other than to initiate measurement of the health condition parameter when the toggle switch is depressed when the steering wheel is in a second state.

\* \* \* \* \*